United States Patent
Imai

(10) Patent No.: US 9,842,395 B2
(45) Date of Patent: Dec. 12, 2017

(54) RADIATION IMAGE PROCESSING DEVICE, RADIATION IMAGE PROCESSING METHOD AND PROGRAM

(71) Applicant: FUJIFILM Corporation, Tokyo (JP)

(72) Inventor: Yoshiro Imai, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/493,469

(22) Filed: Apr. 21, 2017

(65) Prior Publication Data

US 2017/0221207 A1 Aug. 3, 2017

Related U.S. Application Data

(63) Continuation of application No. 14/845,713, filed on Sep. 4, 2015, now Pat. No. 9,704,241, which is a (Continued)

(30) Foreign Application Priority Data

Mar. 28, 2013 (JP) .................................. 2013-067794
Nov. 6, 2013 (JP) .................................. 2013-229940

(51) Int. Cl.
*G06T 9/00* (2006.01)
*G06T 7/00* (2017.01)
(Continued)

(52) U.S. Cl.
CPC .......... *G06T 7/0012* (2013.01); *A61B 6/5282* (2013.01); *G06K 9/4604* (2013.01);
(Continued)

(58) Field of Classification Search
CPC ................. G06T 7/0012; G06T 5/50; G06T 2207/20224; G06T 2207/20221;
(Continued)

(56) References Cited

U.S. PATENT DOCUMENTS 6,385,287 B1 * 5/2002 Dorner ..................... A61B 6/00
378/154
8,064,676 B2 11/2011 Li et al.
(Continued)

OTHER PUBLICATIONS

Fivez et al., "Multi-Resolution Contrast Amplification in Digital Radiography With Compensation for Scattered Radiation", IEEE, 1996, pp. 339-342.
(Continued)

*Primary Examiner* — Amandeep Saini
(74) *Attorney, Agent, or Firm* — Birch, Stewart, Kolasch & Birch, LLP

(57) ABSTRACT

It is possible to allow image processing on a radiation image such that the same effect of scattered radiation elimination as when imaging is actually performed using a grid is obtained. When performing processing for eliminating scattered radiation included in radiation transmitted through a subject M on a radiation image imaged by irradiating the subject M with radiation, a characteristic acquisition unit 32 acquires a virtual grid characteristic as a characteristic of a virtual grid assumed to be used to eliminate scattered radiation at the time of imaging of the radiation image. A scattered radiation elimination unit 36 performs scattered radiation elimination processing of the radiation image based on the virtual grid characteristic.

14 Claims, 5 Drawing Sheets

Related U.S. Application Data continuation of application No. PCT/JP2014/055851, filed on Mar. 6, 2014.

(51) Int. Cl.
   *G06K 9/46* (2006.01)
   *G06T 5/50* (2006.01)
   *A61B 6/00* (2006.01)

(52) U.S. Cl.
   CPC ...... *G06T 5/50* (2013.01); *G06T 2207/10116* (2013.01); *G06T 2207/20221* (2013.01); *G06T 2207/20224* (2013.01); *G06T 2207/30061* (2013.01)

(58) Field of Classification Search
   CPC . G06T 2207/30061; G06T 2207/10116; A61B 6/5282; G06K 9/4604
   USPC ........................................................ 382/132
   See application file for complete search history.

(56) References Cited

U.S. PATENT DOCUMENTS

2005/0002551 A1    1/2005  Takagi
   2013/0156267 A1*   6/2013  Muraoka ................ A61B 6/507
                                                            382/103

OTHER PUBLICATIONS

International Search Report issued in PCT/JP2014/055851, dated Jun. 3, 2014.
Written Opinion of the International Searching Authority issued in PCT/JP2014/055851, dated Jun. 3, 2014.
Extended European Search Report, dated Mar. 30, 2016, for corresponding European Application No. 14773093.1.
Jarry et al., "Characterization of Scattered Radiation in kV CBCT Images Using Monte Carlo Simulations," Medical Physics, vol. 33, No. 11, Nov. 2006 (published Oct. 24, 2006), pp. 4320-4329.
Lazos et al., "Monte Carlo Evaluation of Scatter Mitigation Strategies in Cone-beam CT," Medical Physics, vol. 37, No. 10, Oct. 2010 (published Sep. 28, 2010), pp. 5456-5470.
Maltz et al., "Algorithm for X-ray Scatter, Beam-Hardening, and Beam Profile Correction in Diagnostic (Kilovoltage) and Treatment (Megavoltage) Cone Beam CT," IEEE Transactions on Medical Imaging, vol. 27, No. 12, Dec. 2008 (published Nov. 21, 2008), pp. 1791-1810.
Mohammadi et al., "Proceedings of the Sixteenth EGS Users' Meeting in Japan," Aug. 6-8, 2009 (Jan. 1, 2009), KEK Proceedings 2009—Nov. 6, 2009 R, pp. 1-115 (120 pages).

\* cited by examiner

RADIATION IMAGE PROCESSING DEVICE, RADIATION IMAGE PROCESSING METHOD AND PROGRAM

CROSS REFERENCE TO RELATED APPLICATIONS

This application is a Continuation of copending application Ser. No. 14/845,713 filed on Sep. 4, 2015, which is a Continuation of PCT International Application No. PCT/JP2014/055851 filed on Mar. 6, 2014, and which claims priority under 35 U.S.C. §119(a) to Japanese Patent Application No. 2013-067794 filed in Japan on Mar. 28, 2013, and to Japanese Patent Application No. 2013-229940 filed in Japan on Nov. 6, 2013, the entire contents of all of which are expressly incorporated by reference into the present application.

BACKGROUND OF THE INVENTION

1. Field of the Invention

The present invention relates to a radiation image processing device and a radiation image processing method which perform image processing on a radiation image, and a program which causes a computer to execute the radiation image processing method.

2. Description of the Related Art

In the related art, when imaging a radiation image of a subject with radiation transmitted through the subject, if the thickness of the subject is particularly great, there is a problem in that radiation is scattered inside the subject, and contrast of the acquired radiation image is degraded due to scattered radiation. For this reason, at the time of imaging of a radiation image, a scattered radiation elimination grid (hereinafter, simply referred to as a grid) is disposed between the subject and a radiation detector such that the radiation detector which detects radiation to acquire a radiation image is not irradiated with scattered radiation, and imaging is performed. If imaging is performed using a grid, the radiation detector is hardly irradiated with radiation scattered by the subject, and thus, it is possible to improve contrast of the radiation image.

If imaging using a grid is performed, a thin stripe pattern (moire) corresponding to the grid is included in the radiation image along with a subject image, and thus, an image is hard to view. For this reason, processing for eliminating the stripe pattern due to the grid from the radiation image has been known.

The grid has a configuration in which interspace materials, such as lead not transmitting radiation and aluminum or fiber easily transmitting radiation, are alternately disposed in a fine grating density of, for example, about 4.0 pieces/mm, and thus, is comparatively heavy. In portable imaging which is performed in a patient's room, the grid needs to be disposed between a patient lying on a bed and the radiation detector. For this reason, the burden of work to dispose the grid and the burden of the patient at the time of imaging are great. In the case of a convergence type grid, concentration unevenness may occur in the radiation image due to oblique incidence of radiation. A fine stripe pattern (more) corresponding to the pitch of the grid is recorded in the radiation image along with a subject image, and the radiation image may be hard to view.

Accordingly, processing in which imaging of a radiation image is performed without using a grid, and the effect of image quality improvement with elimination of scattered radiation using a grid is provided to the radiation image through image processing has been suggested (see U.S. Pat. No. 8,064,676B and C Fivez et al, Multi-resolution contrast amplification in digital radiography with compensation for scattered radiation, 1996 IEEE, pp 339-342). In the methods of U.S. Pat. No. 8,064,676B and C Fivez et al, Multi-resolution contrast amplification in digital radiography with compensation for scattered radiation, 1996 IEEE, pp 339-342, a radiation image is frequency-resolved into a plurality of frequency components, scattered radiation elimination processing for controlling contrast or latitude is performed on a low frequency component regarded as a component of scattered radiation, and frequency components after the processing are synthesized to acquire a radiation image with the component of scattered radiation eliminated. In the method described in U.S. Pat. No. 8,064,676B described above, the scattered radiation elimination processing is performed by multiplying the low frequency component by a gain according to the layer of the low frequency component and the pixel value of the low frequency component. The gain is a value less than 1, and has a smaller value for a lower frequency band or a brighter pixel value. In the method described in C Fivez et al, Multi-resolution contrast amplification in digital radiography with compensation for scattered radiation, 1996 IEEE, pp 339-342, a lower frequency band is significantly suppressed in a geometrical progression manner using a table for converting a low frequency component according to the pixel value thereof.

According to the methods of U.S. Pat. No. 8,064,676B and C Fivez et al, Multi-resolution contrast amplification in digital radiography with compensation for scattered radiation, 1996 IEEE, pp 339-342, since a grid is not required at the time of imaging, it is possible to reduce the burden of a patient at the time of imaging and to prevent degradation of image quality due to concentration unevenness and moire.

SUMMARY OF THE INVENTION

On the other hand, the grid is configured to eliminate or absorb scattered radiation in a greater amount than primary radiation being transmitted through the subject and directly irradiating the radiation detector. There are various types of grids, and the scattered radiation elimination performance is different according to the materials forming a grid, such as lead and aluminum, a grating ratio as an aspect ratio in a cross-section, a grating density, or the like. For this reason, in order to obtain the effect of scattered radiation elimination of the grid through image processing, it is necessary to perform scattered radiation elimination processing in which the scattered radiation elimination performance of a virtual grid assumed to be used is reflected.

However, in the methods described in U.S. Pat. No. 8,064,676B and C Fivez et al, Multi-resolution contrast amplification in digital radiography with compensation for scattered radiation, 1996 IEEE, pp 339-342, since the scattered radiation elimination processing is performed according to the pixel value of the low frequency component of the radiation image, the scattered radiation elimination performance of the virtual grid is not reflected in the radiation image acquired through the processing.

When imaging a radiation image using a grid, a comparatively greater amount of radiation is eliminated at a place where the amount of scattered radiation is great, and a great amount of radiation is not eliminated at a place where the amount of scattered radiation is small. Accordingly, image quality of a radiation image acquired through imaging with a grid is different according to the distribution of scattered radiation in radiation transmitted through the subject.

However, in the methods described in U.S. Pat. No. 8,064,676B and C Fivez et al, Multi-resolution contrast amplification in digital radiography with compensation for scattered radiation, 1996 IEEE, pp 339-342, scattered components are eliminated evenly over the entire radiation image according to the pixel value of the low frequency component of the radiation image without consideration of the distribution of scattered radiation. For this reason, a radiation image acquired through actual imaging with a virtual grid and a radiation image acquired through image processing are different in image quality.

Accordingly, when a radiation image acquired through imaging with a grid and a radiation image with scattered components eliminated through image processing using the methods described in U.S. Pat. No. 8,064,676B and C Fivez et al, Multi-resolution contrast amplification in digital radiography with compensation for scattered radiation, 1996 IEEE, pp 339-342 without using a grid are mixed, a physician as an observer needs to perform diagnosis in a state where the radiation images which are different in image quality are mixed. However, if the radiation images which are different in image quality are mixed, the physician may not perform diagnosis accurately.

The invention has been accomplished in consideration of the situation described above, and an object of the invention is to enable image processing to be performed on a radiation image such that the same effect of scattered radiation elimination as when imaging is actually performed using a grid is obtained.

A radiation image processing device according to the invention, which performs processing for eliminating scattered radiation included in radiation transmitted through a subject on a radiation image imaged by irradiating the subject with radiation, includes characteristic acquisition means for acquiring a virtual grid characteristic as a characteristic of a virtual grid assumed to be used to eliminate the scattered radiation at the time of imaging of the radiation image, and scattered radiation elimination means for performing scattered radiation elimination processing of the radiation image based on the virtual grid characteristic.

The radiation image processing device according to the invention may further include scattering information acquisition means for acquiring scattered component information representing a scattered component of radiation included in the radiation image, and the scattered radiation elimination means may be means for performing the scattered radiation elimination processing based on the virtual grid characteristic and the scattered component information.

In the radiation image processing device according to the invention, the scattered radiation elimination means may be means for performing the scattered radiation elimination processing on at least one frequency component among a plurality of frequency components included in the radiation image.

"At least one frequency component" means a frequency component of a frequency band corresponding to the scattered component included in the radiation image.

In the radiation image processing device according to the invention, the characteristic acquisition means may be means for acquiring, as the virtual grid characteristic, at least one of transmittance to the scattered radiation and transmittance to primary radiation included in radiation transmitted through the subject.

In the radiation image processing device according to the invention, the characteristic acquisition means may be means for acquiring the virtual grid characteristic by receiving the designation of the virtual grid characteristic.

In the radiation image processing device according to the invention, the characteristic acquisition means may be means for receiving the designation of the virtual grid characteristic by at least one of grid information representing the type of a grid, information about the subject, and imaging conditions at the time of the acquisition of the radiation image.

In the radiation image processing device according to the invention, the scattered component information may be a scattered radiation content distribution in the radiation image.

In the radiation image processing device according to the invention, the scattering information acquisition means may be means for acquiring the scattered radiation content distribution from the radiation image.

In the radiation image processing device according to the invention, the scattering information acquisition means may be means for acquiring the scattered radiation content distribution based on at least one of information of an irradiation field in the radiation image, information about the subject, and imaging conditions at the time of the acquisition of the radiation image.

In the radiation image processing device according to the invention, the scattered radiation elimination means may be means for performing frequency resolution of the radiation image to acquire a frequency component of each of a plurality of frequency bands, performing the scattered radiation elimination processing on at least one frequency component among the plurality of frequency components, and synthesizing frequency components after the scattered radiation elimination processing and other frequency components to acquire a processed radiation image.

In the radiation image processing device according to the invention, the scattered radiation elimination means may be means for extracting a frequency component of at least one frequency band from the radiation image, performing the scattered radiation elimination processing on the extracted frequency component, and adding or subtracting a frequency component after the processing to or from the radiation image to acquire a processed radiation image.

In the radiation image processing device according to the invention, the characteristic acquisition means may be means for acquiring the virtual grid characteristic for each of the plurality of frequency components.

A radiation image processing method according to the invention, which performs processing for eliminating scattered radiation included in radiation transmitted through a subject on a radiation image imaged by irradiating the subject with radiation, includes acquiring a virtual grid characteristic as a characteristic of a virtual grid assumed to be used to eliminate the scattered radiation at the time of imaging of the radiation image, and performing scattered radiation elimination processing of the radiation image based on the virtual grid characteristic.

The invention may be provided as a program which causes a computer to execute the radiation image processing method according to the invention.

According to the invention, the virtual grid characteristic as a characteristic of a virtual grid assumed to be used to eliminate scattered radiation at the time of imaging of the radiation image is acquired, and the scattered radiation elimination processing of the radiation image is performed based on the virtual grid characteristic. For this reason, it is possible to provide the same effect of scattered radiation elimination as a practical scattered radiation elimination grid to the radiation image. Furthermore, it is possible to make image quality of the radiation image close to image quality of a radiation image acquired through imaging with various types of scattered radiation elimination grids.

The scattered component information is acquired and the scattered radiation component processing is performed based on the scattered component, whereby it is possible to provide the same effect of scattered radiation elimination as a practical scattered radiation elimination grid to the radiation image.

DESCRIPTION OF THE PREFERRED EMBODIMENTS

Figure 1:
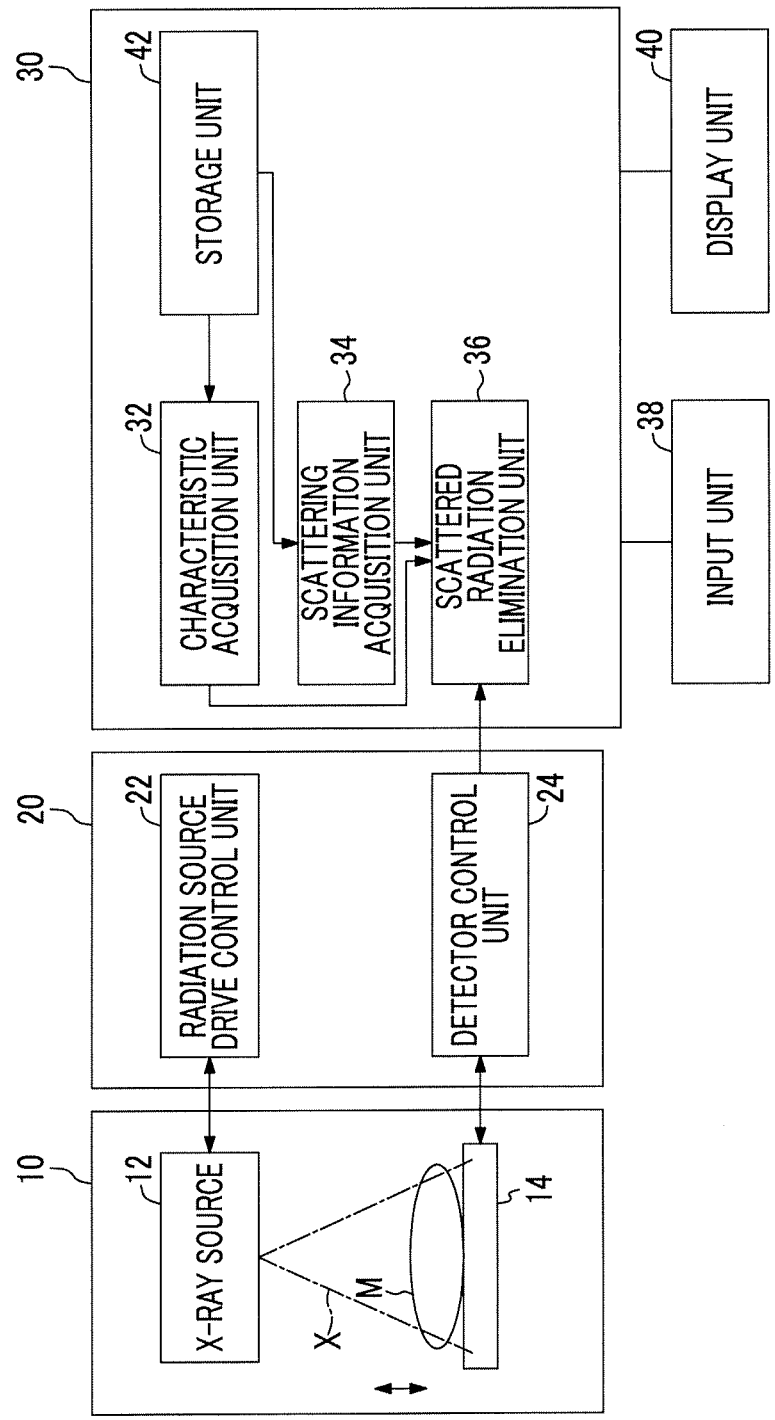
FIG. 1 is a schematic block diagram showing the configuration of a radiation imaging system to which a radiation image processing device according to a first embodiment of the invention is applied.

Hereinafter, an embodiment of the invention will be described referring to the drawings. FIG. 1 is a schematic block diagram showing the configuration of a radiation imaging system to which a radiation image processing device according to a first embodiment of the invention is applied. As shown in FIG. 1, the radiation imaging system of this embodiment includes an imaging device 10, a control device 20 which controls the system, and a radiation image processing device 30.

The imaging device 10 includes an X-ray source 12 which irradiates a subject M with X-rays x, and a radiation detector 14 which detects X-rays transmitted through the subject M to acquire a radiation image of the subject M. In this embodiment, a scattered radiation elimination grid which eliminates scattered radiation scattered by the subject M among the X-rays x transmitted through the subject M is not disposed between the subject M and the radiation detector 14.

The control device 20 includes a radiation source drive control unit 22 which controls driving of the X-ray source 12 according to set imaging conditions, and a detector control unit 24 which controls the radiation detector 14 to acquire a radiation image.

The radiation image processing device 30 includes a characteristic acquisition unit 32 which acquires a virtual grid characteristic as a characteristic of a virtual grid assumed to be used to eliminate scattered radiation at the time of imaging of the radiation image, a scattering information acquisition unit 34 which acquires scattered component information representing a scattered component of X-rays included in the radiation image, a scattered radiation elimination unit 36 which performs scattered radiation elimination processing of the radiation image acquired by the radiation detector 14 based on the virtual grid characteristic acquired by the characteristic acquisition unit 32 and the scattered radiation component information acquired by the scattering information acquisition unit 34, an input unit 38, a display unit 40, and a storage unit 42 which stores various kinds of information. The input unit 38 receives various inputs of an operator on the image processing device 30, for example, the designation of characteristic of a virtual grid described below. Specifically, the input unit 38 is constituted of a keyboard, a mouse, a touch panel, and the like. The display unit 40 is constituted of a CRT, a liquid crystal display, or the like, and assists various inputs necessary for the radiation image acquired by the imaging device 10 and scattered radiation elimination processing described below.

The characteristic acquisition unit 32, the scattering information acquisition unit 34, the scattered radiation elimination unit 36, the input unit 38, the display unit 40, and the storage unit 42 described above can be constituted of, for example, a computer system, such as a general personal computer.

The radiation image processing device 30 has a processor, such as a central processing unit (CPU), and a memory, and the memory stores programs, data, and the like which are necessary when the radiation image processing device 30 controls the respective constituent elements.

The memory of the radiation image processing device 30 may be constituted of a non-transitory and computer-readable storage medium. The computer-readable storage medium is a portable medium, such as a magneto-optical disk, a ROM, a CD-ROM, or a flash memory, or a storage device, such as a hard disk embedded in a computer system. The storage medium may hold programs dynamically for a short period of time or may hold programs for a given period of time.

The radiation image processing device 30 reads and executes the programs stored in the memory, thereby realizing the functions of the characteristic acquisition unit 32, the scattering information acquisition unit 34, and the scattered radiation elimination unit 36.

In this embodiment, the radiation image processing device 30 performs image processing on the radiation image acquired through imaging without using a grid such that the same effect of scattered radiation elimination as when a grid is actually used is provided. Unlike the methods described in U.S. Pat. No. 8,064,676B and C Fivez et al, Multi-resolution contrast amplification in digital radiography with compensation for scattered radiation, 1996 IEEE, pp 339-342, the radiation image processing device 30 performs scattered radiation elimination processing based on the virtual grid characteristic. The characteristic acquisition unit 32 acquires the virtual grid characteristic by an input of the operator from the input unit 38. In this embodiment, it is assumed that the "virtual grid characteristic" is scattered radiation transmittance Ts about the virtual grid and transmittance (primary radiation transmittance) Tp of primary radiation being transmitted through the subject M and directly irradiating the radiation detector 14. The scattered radiation transmittance Ts and the primary radiation transmittance Tp have values of 0 to 1.

In this embodiment, the characteristic acquisition unit 32 acquires the virtual grid characteristic (that is, scattered radiation transmittance Ts and primary radiation transmittance Tp) by receiving the designation of at least one of grid information representing the type of a grid, information (subject information) about the subject, and imaging conditions at the time of the acquisition of the radiation image. The characteristic acquisition unit 32 may acquire the virtual grid characteristic by directly receiving the input of the values of the scattered radiation transmittance Ts and the primary radiation transmittance Tp.

The "grid information" includes at least one of information for specifying the type of a grid, such as a grid ratio, grid density, a convergence type or a parallel type, a focusing distance in a convergence type, and an interspace material (aluminum, fiber, Bakelite, or the like). The scattered radiation transmittance Ts and the primary radiation transmittance Tp are different according to the type of a grid. For this reason, in regard to the grid information, a table in which at least one of various kinds of grid information is associated with the virtual grid characteristic is stored in the storage unit 42.

The "subject information" includes the type of a subject, such as chest, abdomen, or head. At the time of imaging of a radiation image, in general, the type of a grid to be used is determined according to an imaging region, and the scattered radiation transmittance Ts and the primary radiation transmittance Tp are different according to the type of a grid. For this reason, in regard to the subject information, a table in which various kinds of subject information are associated with the virtual grid characteristic is stored in the storage unit 42.

The "imaging conditions" include at least one of an imaging distance (SID) at the time of imaging, an imaging dose, a tube voltage, a target of a radiation source, a material of a filter, the type of a radiation detector used for imaging, and the like. In general, at the time of imaging of the radiation image, the type of a grid to be used is determined according to the imaging conditions, and the scattered radiation transmittance Ts and the primary radiation transmittance Tp are different according to the type of a grid. For this reason, in regard to the imaging conditions, a table in which at least one of various imaging conditions is associated with the virtual grid characteristic is stored in the storage unit 42. In many cases, various imaging conditions are determined according to a facility where the radiation imaging system is installed. For this reason, when imaging conditions at the time of actual imaging are unknown, the imaging conditions according to a facility may be used.

The characteristic acquisition unit 32 acquires the virtual grid characteristic based on at least one of the grid information, the subject information, and the imaging conditions input from the input unit 38 with reference to the tables stored in the storage unit 42. In regard to the grid information, the subject information, and the imaging conditions, an input can be directly received from the input unit 38. A list of various kinds of grid information, various kinds of subject information, and various imaging conditions may be displayed on the display unit 40, the input of the grid information, the subject information, and the imaging conditions may be performed by receiving the selection of at least one of the grid information, the subject information, and the imaging conditions from the list. The imaging conditions may be acquired from the radiation source drive control unit 22.

When the imaging condition is an imaging dose, an acrylic model having a known thickness may be imaged along with the subject, and the imaging dose may be acquired based on the concentration of the portion of the acrylic model in the acquired radiation image. In this case, a table in which the concentration of the acrylic model is associated with the imaging dose may be stored in the storage unit 42, and the imaging dose may be acquired based on the concentration of the acrylic model with reference to the table. When a void area is included in the radiation image, the imaging dose may be acquired based on the concentration of the void area. In this case, a table in which the concentration of the void area is associated with the imaging dose may be stored in the storage unit 42, and the imaging dose may be acquired based on the concentration of the void area with reference to the table. The "void area" means an image area which is obtained by directly irradiating the radiation detector 14 with X-rays without being transmitted through the subject. The imaging dose may be measured using a dosimeter, and the measured imaging dose may be used as the imaging condition.

In this embodiment, as described below, the scattered radiation elimination processing is performed by frequency resolution of the radiation image. In this embodiment, the virtual grid characteristic is acquired for each of a plurality of frequency bands of the radiation image obtained by frequency resolution. For this reason, in the table stored in the storage unit 42, the virtual grid characteristic is associated with each of a plurality of frequency bands.

A table in which all of the grid information, the subject information, and the imaging conditions are associated with the virtual grid characteristic may be stored in the storage unit 42, and the virtual grid characteristic may be acquired based on the grid information, the subject information, and the imaging condition. In this case, the table becomes at least a four-dimensional table in which various kinds of grid information, various kinds of subject information, and various imaging conditions are associated with the virtual grid characteristic.

An exposure magnification factor which is an increase rate of an irradiation dose increasing with the use of a grid, a contrast improvement coefficient which is the ratio of contrast between when a grid is used and when a grid is not used, and selectivity which is the ratio of primary X-rays transmittance to scattered X-rays transmittance are characteristic values representing the characteristic of a grid. The scattered radiation transmittance Ts and the primary radiation transmittance Tp can be calculated from the characteristic values. For this reason, in the characteristic acquisition unit 32, the virtual grid characteristic (that is, the scattered radiation transmittance Ts and the primary radiation transmittance Tp) may be calculated and acquired by receiving the designation of at least one of the exposure magnification factor, the contrast improvement coefficient, and the selectivity.

In this embodiment, the image processing device 30 performs the scattered radiation elimination processing based on the scattered component information as well as the virtual grid characteristic. The image processing device 30 performs the scattered radiation elimination processing based on the virtual grid characteristic and the scattered component information. For this reason, the scattering information acquisition unit 34 acquires the scattered component information. In this embodiment, it is assumed that the scattered component information is a scattered radiation content distribution in the radiation image. In the scattered radiation content distribution, for example, when the subject M is a chest, the amount of scattered radiation is greater in the central portion of the radiation image where a mediastinum exists, and the amount of scattered radiation is smaller in the peripheral portion where a lung field exists.

The scattering information acquisition unit 34 analyzes the radiation image acquired by imaging to acquire the scattered component information (that is, the scattered radiation content distribution). The analysis of the radiation image is performed based on irradiation field information, the subject information, and the imaging conditions at the time of imaging of the radiation image.

The irradiation field information is information representing an irradiation field distribution relating to the position and size of the irradiation field included in the radiation image when imaging is performed using an irradiation field diaphragm. The subject information is information relating to the position on the radiation image of the subject, the distribution of the composition of the subject, the size of the subject, the thickness of the subject, and the like in addition to the type of the subject, such as chest, abdomen, or head. The imaging conditions are information relating to an imaging dose (tube current×irradiation time) at the time of imaging, a tube voltage, an imaging distance (the total of the distance between the X-ray source and the subject and the distance between the subject and the radiation detector), an air gap amount (the distance between the subject and the radiation detector), the characteristics of the radiation detector, and the like. The irradiation field information, the subject information, and the imaging conditions are factors for determining the distribution of scattered radiation included in the radiation image. For example, the amount of scattered radiation depends on the magnitude of the irradiation field, when the thickness of the subject is greater, the amount of scattered radiation becomes greater, and if there is air between the subject and the radiation detector, the amount of scattered radiation is decreased. Therefore, with the use of the information, it is possible to more accurately acquire the scattered radiation content distribution.

The scattering information acquisition unit 34 calculates a primary radiation image and a scattered radiation image from a distribution $T(x,y)$ of the subject thickness in the radiation image acquired through imaging according to Expressions (1) and (2) described below and calculates a scattered radiation content distribution $S(x,y)$ from the calculated primary radiation image and scattered radiation image based on Expression (3). The scattered radiation content distribution $S(x,y)$ has a value of 0 to 1.

$$Ip(x,y)=Io(x,y)\times\exp(-\mu\times T(x,y)) \quad (1)$$

$$Is(x,y)=Io(x,y)*S\sigma(T(x,y)) \quad (2)$$

$$S(x,y)=Is(x,y)/(Is(x,y)+Ip(x,y)) \quad (3)$$

$(x,y)$ are the coordinates of a pixel position of the radiation image, $Ip(x,y)$ is a primary radiation image at the pixel position $(x,y)$, $Is(x,y)$ is a scattered radiation image at the pixel position $(x,y)$, $Io(x,y)$ is an incidence dose to the subject surface at the pixel position $(x,y)$, $\mu$ is a radiation attenuation coefficient of the subject, and $S\sigma(T(x,y))$ is a convolution kernel representing the characteristic of scattering according to the subject thickness at the pixel position $(x,y)$. Expression (1) is an expression based on a known exponential attenuation rule, and Expression (2) is an expression based on the method described in "J M Boon et al, An analytical model of the scattered radiation distribution in diagnostic radiolog, Med. Phys. 15(5), September/October 1988" (Reference Document 1). Even if the incidence dose $Io(x,y)$ to the subject surface is defined as any value, the incidence dose $Io(x,y)$ is cancelled by division when calculating $S(x,y)$, and thus, the incidence dose $Io(x,y)$ may be set to an arbitrary value, for example, 1.

The distribution $T(x,y)$ of the subject thickness may be calculated by assuming that the luminance distribution in the radiation image substantially matches the distribution of the thickness of the subject and converting the pixel value of the radiation image to the thickness using the radiation attenuation coefficient value. In place of this, the thickness of the subject may be measured using a sensor or the like, or may be approximated by a model, such as a cube or an elliptic cylinder.

In Expression (2), * is an operator representing a convolution operation. The property of a kernel changes depending on the distribution of the irradiation field, the distribution of the composition of the subject, the irradiation dose at the time of imaging, the tube voltage, the imaging distance, the air gap amount, the characteristics of the radiation detector, and the like, in addition to the thickness of the subject. According to the method described in Reference Document 1, scattered radiation can be approximated by convolution of a point spread function (in Expression (2), $S\sigma(T(x,y))$) to primary radiation. $S\sigma(T(x,y))$ can be obtained experimentally according to the irradiation field information, the subject information, the imaging conditions, and the like.

In this embodiment, $S\sigma(T(x,y))$ may be calculated based on the irradiation field information, the subject information, and the imaging conditions at the time of imaging. A table in which various kinds of irradiation field information, various kinds of subject information, and various imaging conditions are associated with $S\sigma(T(x,y))$ may be stored in the storage unit 42, and $S\sigma(T(x,y))$ may be obtained based on the irradiation field information, the subject information, and the imaging conditions at the time of imaging with reference to the table. $S\sigma(T(x,y))$ may be approximated by $T(x,y)$.

The scattered radiation elimination unit 36 performs the scattered radiation elimination processing by reducing the frequency components of the frequency bands regarded as scattered radiation in the radiation image based on the virtual grid characteristic and the scattered component information. The scattered radiation elimination unit 36 performs frequency resolution of the radiation image to acquire a frequency component of each of a plurality of frequency bands, performs processing for reducing a gain of at least one frequency component, and synthesizes the processed frequency component and other frequency components to acquire a radiation image subjected to the scattered radiation elimination processing. As a method of frequency resolution, in addition to a method of performing multiplex resolution transform on the radiation image, known arbitrary methods, such as wavelet transform and Fourier transform, can be used.

The scattered radiation elimination unit 36 calculates the conversion coefficient $R(x,y)$ for converting the frequency component from the scattered radiation transmittance Ts and the primary radiation transmittance Tp as the virtual grid characteristic and the scattered radiation content distribution $S(x,y)$ as the scattered component information by Expression (4) described below.

$$R(x,y)=S(x,y)\times Ts+(1-S(x,y))\times Tp \quad (4)$$

Since the scattered radiation transmittance Ts, the primary radiation transmittance Tp, and the scattered radiation content distribution $S(x,y)$ have values of 0 to 1, the conversion coefficient $R(x,y)$ also has a value of 0 to 1. The scattered radiation elimination unit 36 calculates the conversion coefficient $R(x,y)$ for each of a plurality of frequency bands.

In the following description, the pixel value of the radiation image is referred to as $I(x,y)$, a frequency component image obtained by frequency resolution is referred to as $I(x,y,r)$, frequency synthesis is referred to as $I(x,y)=\Sigma rI(x,y,r)$, the conversion coefficient of each frequency band is referred to as $R(x,y,r)$, and the scattered radiation transmittance and the primary radiation transmittance of each frequency band are referred to as $Ts(r)$ and $Tp(r)$. r represents the layer of the frequency band, and when r is greater, the frequency is lower. Accordingly, $I(x,y,r)$ becomes a frequency component image of a certain frequency band. The scattered radiation content distribution $S(x,y)$ about the radiation image may be used as is, or similarly to the scattered radiation transmittance Ts and the primary radiation transmittance Tp, the scattered radiation content distribution S(x,y) may be acquired for each frequency band.

In this embodiment, the conversion coefficient R(x,y,r) is calculated for each frequency component, the pixel value of the frequency component image I(x,y,r) is converted by multiplying the frequency component image I(x,y,r) by the conversion coefficient R(x,y,r) of the corresponding frequency band, and the frequency component image I(x,y,r) (that is, I(x,y,r)×R(x,y,r)) multiplied by the conversion coefficient R(x,y,r) is frequency-synthesized to acquire a processed radiation image I'(x,y). Accordingly, the processing which is performed in the scattered radiation elimination unit 36 is represented by Expression (5) described below. Since the conversion coefficient R(x,y,r) has a value of 0 to 1, the pixel value of the frequency component at the pixel position (x,y), that is, the gain is reduced by multiplying the frequency component (x,y,r) by the conversion coefficient R(x,y,r) of the corresponding frequency band.

$$I'(x, y) = \Sigma r\{I(x, y, r) \times R(x, y, r)\} \quad (5)$$
$$= \Sigma r\{I(x, y, r) \times (S(x, y) \times Ts(r) + (1 - S(x, y)) \times Tp(r))\}$$

In this embodiment, the radiation image is frequency-resolved into six frequency bands, and the scattered radiation transmittance Ts and the primary radiation transmittance Tp are acquired for the six frequency bands. In this case, the scattered radiation transmittance Ts and the primary radiation transmittance Tp have, for example, values shown in Expression (6) described below. In Expression (6), it is assumed that the value represents a lower frequency band toward the right side.

$$Ts = \{0.7, 0.7, 0.7, 0.7, 0.3, 0.2\}$$
$$Tp = \{0.7, 0.7, 0.7, 0.7, 0.7, 0.7\} \quad (6)$$

As shown in Expression (6), while the scattered radiation transmittance Ts and the primary radiation transmittance Tp have the same value in a high frequency band (r=1 to 4), in a low frequency band (r=5 to 6), the scattered radiation transmittance Ts has a lower value. This is because a grid has a high elimination rate in a low frequency band, in which the frequency component of scattered radiation is dominant, but has a small frequency dependence of the elimination rate for primary radiation.

Figure 2:
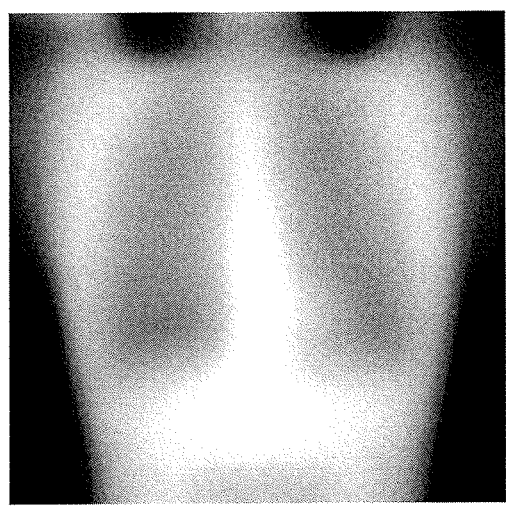
FIG. 2 is a diagram showing a scattered radiation content distribution in a radiation image of a chest.
Figure 3:
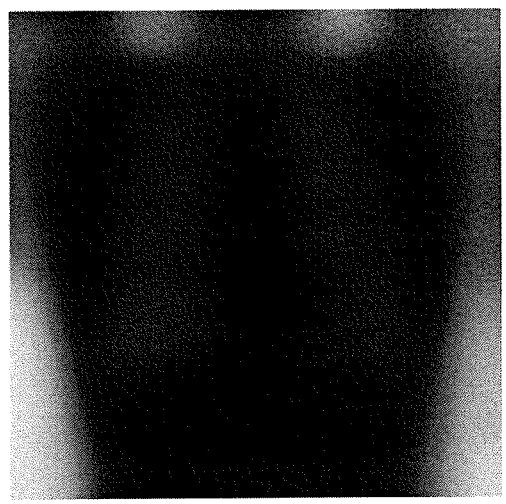
FIG. 3 is a diagram showing a conversion coefficient calculated when indicating the scattered radiation content distribution shown in FIG. 2.

FIG. 2 is a diagram showing a scattered radiation content distribution S(x,y) in a radiation image of a chest. In FIG. 2, the higher the scattered radiation content distribution S(x,y), the higher the luminance at each pixel position. From FIG. 2, it is understood that, in the image of the chest, the content of scattered radiation in a mediastinal portion and around a lung field is high. When indicating the scattered radiation content distribution S(x,y), the conversion coefficient calculated based on Expressions (4) and (6) is shown in FIG. 3. In FIG. 3, when luminance is low, the value of the conversion coefficient is small, and the pixel value of the radiation image is reduced more greatly. When comparing FIGS. 2 and 3, it is understood that the value of the conversion coefficient becomes small in the mediastinal portion and around the lung field where the content of scattered radiation is high. Accordingly, in the processed radiation image acquired by performing the processing shown in Expression (5) using the conversion coefficient calculated in the above-described manner, a scattered radiation component is eliminated according to the type of a grid assumed to be used.

Scattered radiation elimination unit 36 may eliminate scattered radiation of the radiation image as follows. First, similarly as above, if frequency synthesis is represented by I(x,y)=ΣrI(x,y,r), the scattered radiation elimination unit 36 resolves the frequency component image I(x,y,r) into a scattered radiation component Is(x,y,r) and a primary radiation component Ip(x,y,r) using the scattered radiation content distribution S(x,y) by Expression (7) described below.

$$Is(x,y,r) = S(x,y) \times I(x,y,r)$$
$$Ip(x,y,r) = (1-S(x,y)) \times I(x,y,r) \quad (7)$$

The scattered radiation elimination unit 36 performs image conversion by applying the scattered radiation transmittance Ts(r) and the primary radiation transmittance Tp(r) as the virtual grid characteristic respectively to the scattered radiation component Is(x,y,r) and the primary radiation component Ip(x,y,r) by Expression (8) described below, and calculates converted scattered radiation component Is'(x,y,r) and primary radiation component Ip'(x,y,r).

$$Is'(x,y,r) = Is(x,y,r) \times Ts(r) = S(x,y) \times I(x,y,r) \times Ts(r)$$
$$Ip'(x,y,r) = Ip(x,y,r) \times Tp(r) = (1-S(x,y)) \times I(x,y,r) \times Tp(r) \quad (8)$$

Is'(x,y,r) and the primary radiation component Ip'(x,y,r) are frequency-synthesized by Expression (9) described below to calculate the processed radiation image I(x,y)'.

$$I'(x, y) = \Sigma r\{Is'(x, y, r) \times Ip'(x, y, r)\} \quad (9)$$
$$= \Sigma r\{S(x, y) \times I(x, y, r) \times Ts(r) + (1 - S(x, y)) \times I(x, y, r) \times Tp(r)\}$$
$$= \Sigma r\{I(x, y, r) \times (S(x, y) \times Ts(r) + (1 - S(x, y)) \times Tp(r))\}$$

Figure 4:
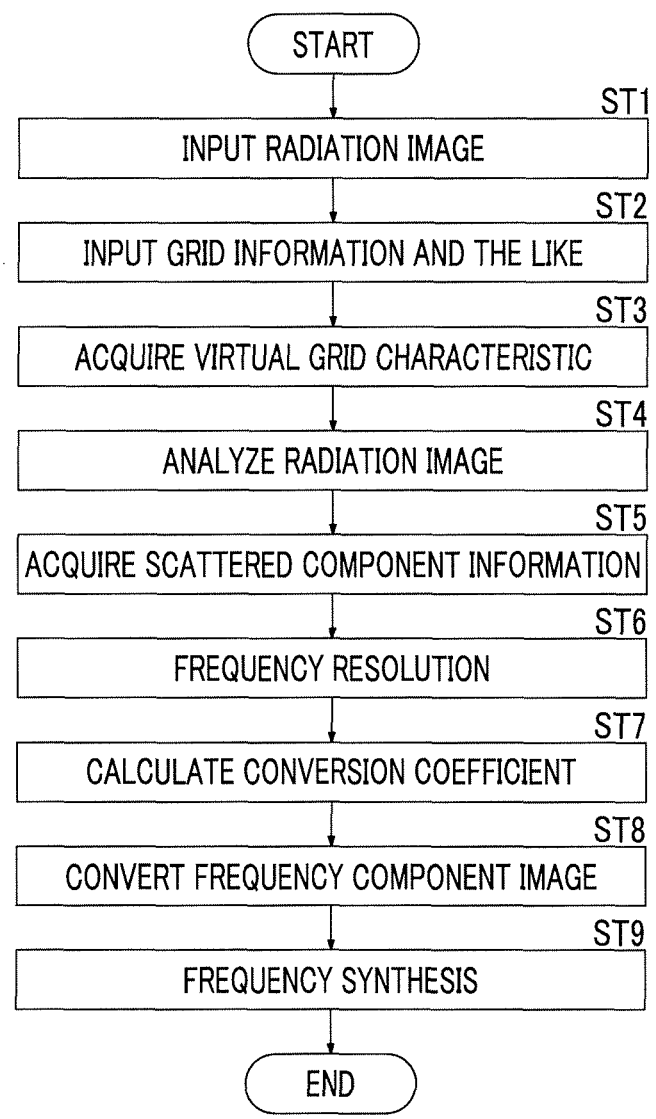
FIG. 4 is a flowchart showing processing which is performed in the first embodiment.

Next, processing which is performed in the first embodiment will be described. FIG. 4 is a flowchart showing processing which is performed in the first embodiment. If the radiation image acquired in the imaging device 10 is input to the image processing device 30 (Step ST1), the characteristic acquisition unit 32 receives the input of at least one of the grid information, the subject information, and the imaging conditions from the input unit 38 (grid information and the like input, Step ST2), and acquires the virtual grid characteristic (that is, the scattered radiation transmittance Ts and the primary radiation transmittance Tp) (Step ST3).

Next, the scattering information acquisition unit 34 analyzes the radiation image (Step ST4), and acquires the scattered radiation component information (that is, the scattered radiation content distribution S(x,y)) (Step ST5). The scattered radiation elimination unit 36 performs frequency resolution of the radiation image (Step ST6). The processing of Steps ST2 and ST3, the processing of Steps ST4 and ST5, and the processing of Step ST6 may be performed in parallel, the processing of Steps ST4 and ST5 may be performed earlier, or the processing of Step ST6 may be performed earlier.

The scattered radiation elimination unit 36 calculates the conversion coefficient R(x,y,r) for each frequency band by Expression (4) described above (Step ST7), and converts the frequency component image I(x,y,r) by the conversion coefficient R(x,y,r) (Step ST8). The converted frequency component image I'(x,y,r) is frequency-synthesized to acquire the processed radiation image (Step ST8), and the processing ends. The processed radiation image is displayed on the display unit 40 and provided for diagnosis, or is transmitted to and stored in an external image server.

In this way, in the first embodiment, the virtual grid characteristic as the characteristic of the grid assumed to be used to eliminate scattered radiation at the time of imaging of the radiation image is acquired, the scattered component information is further acquired, and the scattered radiation elimination processing of the radiation image is performed based on the virtual grid characteristic and the scattered radiation component information. For this reason, it is possible to provide the same effect of scattered radiation elimination as a practical scattered radiation elimination grid to the radiation image. Furthermore, it is possible to make image quality of the radiation image close to image quality of a radiation image acquired through imaging with various types of scattered radiation elimination grids.

When a convergence type grid is used, concentration unevenness may occur in the radiation image due to oblique incidence of radiation. Meanwhile, in the first embodiment, since concentration unevenness due to oblique incidence of radiation does not occur, it is possible to acquire a higher-quality radiation image.

Next, a second embodiment of the invention will be described. In the second embodiment, the configuration of the image processing device is the same as that in the first embodiment, and only different processing is performed. For this reason, detailed description of the device will be omitted. In the first embodiment described above, the radiation image is frequency-resolved, and the frequency component image after conversion is frequency-synthesized to acquire the processed radiation image. Meanwhile, in the second embodiment, a processed radiation image is acquired by extracting a frequency component of a frequency band to be eliminated from a radiation image, performing scattered radiation elimination processing on the extracted frequency component, and adding or subtracting a frequency component after processing to or from the radiation image. From this point, the second embodiment is different from the first embodiment.

In the second embodiment, the scattered radiation elimination unit 36 performs processing as follows. First, as in the first embodiment, a radiation image is frequency-resolved to acquire a frequency component image I(x,y,r), and a conversion coefficient R'(x,y,r) for elimination is calculated for each frequency band by Expression (10) described below.

$$R'(x,y) = S(x,y) \times (1 - Ts(r)) + (1 - S(x,y)) \times (1 - Tp(r)) \quad (10)$$

An elimination component $\Delta I(x,y,r)$ of each frequency band is calculated by Expression (11) described below.

$$\Delta I(x, y, r) = I(x, y, r) \times R'(x, y, r) \quad (11)$$
$$= I(x, y, r) \times \{S(x, y) \times (1 - Ts(r)) + (1 - S(x, y)) \times (1 - Tp(r))\}$$

The elimination component $\Delta I(x,y,r)$ is frequency-synthesized, and the frequency-synthesized elimination component $\Sigma r \Delta I(x,y,r)$ is subtracted from the radiation image I(x,y) to acquire a processed radiation image I'(x,y).

$$I'(x, y) = I(x, y) - \Sigma r \Delta I(x, y, r) \quad (12)$$
$$= I(x, y) - \Sigma r \{I(x, y, r) \times \{S(x, y) \times (1 - Ts(r)) + (1 - S(x, y)) \times (1 - Tp(r))\}\}$$

Figure 5:
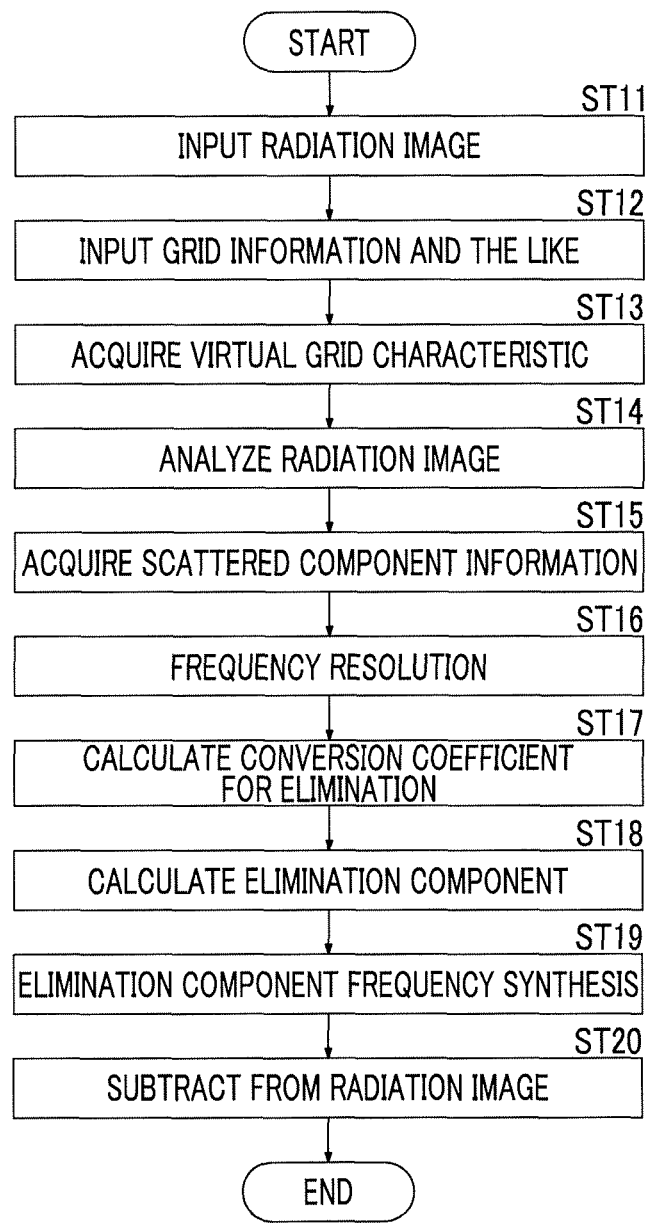
FIG. 5 is a flowchart showing processing which is performed in a second embodiment.

Next, processing which is performed in the second embodiment will be described. FIG. 5 is a flowchart showing processing which is performed in the second embodiment. The processing of Steps ST11 to ST16 is the same as the processing of Steps ST1 to ST6 in the first embodiment, and thus detailed description thereof will be omitted.

After Step ST16, the scattered radiation elimination unit 36 calculates the conversion coefficient R'(x,y,r) for elimination for each frequency band by Expression (10) described above (Step ST17), and calculates the elimination component $\Delta I(x,y,r)$ of each frequency band by Expression (11) described above (Step ST18). The elimination component $\Delta I(x,y,r)$ is frequency-synthesized (Step ST19), and the frequency-synthesized elimination component $\Sigma r \Delta I(x,y,r)$ is subtracted from the radiation image to acquire the processed radiation image (Step ST20), and the processing ends. The processed radiation image is displayed on the display unit 40 and provided for diagnosis, or is transmitted to and stored in an external image server.

In the second embodiment described above, the scattered radiation elimination unit 36 may eliminate scattered radiation of the radiation image as follows. First, similarly as above, if frequency resolution is represented by $I(x,y) = \Sigma r I(x,y,r)$, the frequency component image I(x,y,r) is resolved into a scattered radiation component Is(x,y,r) and a primary radiation component Ip(x,y,r) using the scattered radiation content distribution S(x,y) by Expression (7) described above. Image conversion is performed by applying the scattered radiation transmittance Ts(r) and the primary radiation transmittance Tp(r) as the virtual grid performance respectively to the scattered radiation component Is(x,y,r) and the primary radiation component Ip(x,y,r) by Expression (13) described below, and a scattered radiation elimination component $\Delta Is(x,y,r)$ and a primary radiation elimination component $\Delta Ip(x,y,r)$ are calculated.

$$\Delta Is(x,y,r) = Is(x,y) \times (1 - Ts(r)) = S(x,y) \times I(x,y) \times (1 - Ts(r))$$

$$\Delta Ip(x,y,r) = Ip(x,y) \times (1 - Tp(r)) = (1 - S(x,y)) \times I(x,y) \times (1 - Tp(r)) \quad (13)$$

The scattered radiation elimination component $\Delta Is(x,y,r)$ and the primary radiation elimination component $\Delta Ip(x,y,r)$ are frequency-synthesized by Expression (14) described below, and the frequency-synthesized scattered radiation elimination component $\Sigma r \Delta Is(x,y,r)$ and primary radiation elimination component $\Sigma r \Delta Ip(x,y,r)$ are subtracted from the radiation image to calculate the processed radiation image I'(x,y).

$$I'(x,y) = I(x,y) - \Sigma r(\Delta Is(x,y,r) + \Delta Ip(x,y,r)) \quad (14)$$

In the first and second embodiments described above, it is preferable that the scattered radiation elimination processing is performed in a space where the radiation image has a pixel value proportional to the incidence dose to the radiation detector (a linear space with respect to a radiation dose), and then, logarithmic conversion is performed to convert the space to a logarithmic-linear space proportional to a human's visual sense.

In the first and second embodiments described above, although the characteristic acquisition unit 32 acquires the scattered radiation transmittance Ts and the primary radiation transmittance Tp as the virtual grid characteristic, the invention is not limited thereto, and the characteristic acquisition unit 32 may acquire only one of the scattered radiation transmittance Ts and the primary radiation transmittance Tp.

In the first and second embodiments described above, although the scattered radiation elimination processing is performed on the radiation image acquired through imaging without using a grid, a radiation image acquired through imaging with a grid may be processed. In this case, processing for eliminating a stripe pattern due to a grid is performed on the radiation image, and then, the scattered radiation elimination processing is performed. The scattered radiation elimination processing may be performed as follows. A radiation image (first grid-use image) imaged using a first grid as a desired grid is acquired. A virtual grid characteristic corresponding to a desired virtual grid is acquired. A scattered radiation dose and a primary radiation dose in the acquired first grid-use image are converted so as to become a scattered radiation dose and a primary radiation dose of a grid (a grid having the scattered radiation transmittance and the primary radiation transmittance of the acquired virtual grid characteristic) corresponding to the acquired virtual grid characteristic. Both of the first grid and the grid corresponding to the virtual grid characteristic may have a high scattered radiation elimination effect, or arbitrary selection may be made according to the purpose or situation. As the processing for eliminating a stripe pattern due to a grid, for example, a method described in JP2012-203504A can be used.

A processed radiation image obtained by applying one virtual grid characteristic (first virtual grid characteristic) to a radiation image imaged with no grid and subjecting the radiation image to the scattered radiation elimination processing may be subjected to the scattered radiation elimination processing in this embodiment. In this case, the scattered radiation elimination processing may be performed as follows. First, the first virtual grid characteristic and a first processed radiation image which is the processed radiation image applied with the first virtual grid characteristic are acquired. Next, a second virtual grid characteristic which is different from the first virtual grid characteristic and corresponds to a desired virtual grid is acquired. A scattered radiation dose and a primary radiation dose in the first processed radiation image are converted so as to become a scattered radiation dose and a primary radiation dose corresponding to the second virtual grid characteristic based on the second virtual grid characteristic. Both of the first virtual grid characteristic and the second virtual grid characteristic may have a high scattered radiation elimination effect, or arbitrary selection may be made according to the purpose or situation.

Such processing is performed, whereby it is possible to virtually acquire a processed radiation image as if imaging is performed using a grid having a grid ratio different from the used grid. For example, a processed radiation image is virtually acquired based on a radiation image (or the first processed radiation image obtained by subjecting the radiation image imaged with no grid to the scattered radiation elimination processing based on the first virtual grid characteristic) imaged using a grid having a grid ratio of 3:1 as if imaging is performed using a grid having a grid ratio of 10:1. Conversely, a processed radiation image is acquired based on a radiation image (or the first processed radiation image obtained by subjecting the radiation image imaged with no grid to the scattered radiation elimination processing based on the first virtual grid characteristic) imaged using a grid having a grid ratio of 10:1 as if imaging is performed using a grid having a grid ratio of 3:1.

In these cases, even if imaging of the subject is not repeated, it is possible to easily acquire a radiation image with a converted grid ratio. For this reason, it is possible to obtain a processed radiation image subjected to the scattered radiation elimination processing from a radiation image with an unintended grid ratio or the first processed radiation image described above using a grid having a desired grid ratio. Accordingly, it is possible to meet a demand for observing processed radiation images subjected to the scattered radiation elimination processing with different degrees without reimaging the subject. When acquiring images subjected to the scattered radiation elimination processing with different degrees, the labor of reimaging is saved.

As a specific method, for example, in the first embodiment, a table in which each combination of pre-conversion grid information corresponding to a grid before conversion and post-conversion grid information corresponding to a grid after conversion is associated to $S\sigma$ representing the characteristic of scattering in Expression (2) is stored in the storage unit 42. In the table, it is assumed that $S\sigma$ is obtained in advance by an experiment or the like such that the characteristic of scattering by the grid before conversion can be relatively converted to the characteristic of scattering by the grid after conversion. The scattered radiation information acquisition unit 34 acquires first grid information corresponding to an actually used grid (or a virtual grid) as the pre-conversion grid information, acquires second grid information corresponding to a desired virtual grid as the post-conversion grid information, and acquires $S\sigma$ corresponding to the first grid information and the second grid information based on the table. $Io(x,y)$ is set to, for example, 1, and the primary radiation image $Ip(x,y)$ and the scattered radiation image $Is(x,y)$ are calculated using the acquired $S\sigma$ by Expressions (1) and (2). The scattered radiation content distribution $S(x,y)$ may be calculated based on the calculated primary radiation image $Ip(x,y)$ and the scattered radiation image $Is(x,y)$ by Expression (3).

The scattered radiation elimination unit 36 acquires a first grid characteristic (primary radiation transmittance Tp1 and scattered radiation transmittance Ts1) corresponding to the actually used grid (or the virtual grid) and a second virtual grid characteristic (primary radiation transmittance Tp2 and scattered radiation transmittance Ts2) corresponding to the desired virtual grid with respect to the scattered radiation transmittance Ts and the primary radiation transmittance Tp of each frequency band shown in Expression (6). Next, the scattered radiation elimination unit 36 acquires "Tp2/Tp1" as the primary radiation transmittance Tp in Expression (6) and acquires "Ts2/Ts1" as the scattered radiation transmittance Ts in the Expression (6) in order to relatively convert the characteristic of scattering by the first grid before conversion to the characteristic of scattering by the second grid after conversion. The scattered radiation elimination unit 36 may apply the acquired scattered radiation transmittance Ts (=Ts2/Ts1) and primary radiation transmittance Tp (=Tp2/Tp1) to Expression (4) to obtain the conversion coefficient R, and as in the first embodiment, may perform the scattered radiation elimination processing using the conversion coefficient R. In Expression (4) described above, there is a case where the conversion coefficient $R(x,y)$ has a value greater than 1 when the scattered radiation transmittance Ts2 of the second grid characteristic is greater than the scattered radiation transmittance Ts1 of the first grid characteristic.

The first grid characteristic and the second grid characteristic may be acquired by an arbitrary method. For example, a table in which a grid characteristic (primary radiation transmittance Tp and scattered radiation transmittance Ts) obtained in advance by an experiment or the like is associated with each piece of grid information is prepared and stored in the storage unit 42. Next, the scattered radiation elimination unit 36 acquires first and second grid information. The scattered radiation elimination unit 36 acquires the first grid characteristic and the second grid characteristic corresponding to the first and second grid information based on the table stored in the storage unit 42. The first and second grid characteristics may be acquired based on a user input from the input unit 38. The grid information may be acquired by an input from the input unit 38, or for example, as described in JP2003-260053A, grid information may be acquired by forming a protrusion according to the type of a grid in a grid and detecting the protrusion.

There is a case where, depending on an imaging region, imaging is performed without using a scattered radiation elimination grid. It is not preferable to subject a radiation image acquired by imaging such a region to the scattered radiation elimination processing of the first and second embodiments described above. For this reason, it is possible to switch on/off the scattered radiation elimination processing of this embodiment according to an imaging region. Information of an imaging region may be acquired by an input of the operator, may be automatically acquired from an imaging request input to a known console PC (not shown) which controls an imaging flow, or information which is stored in the system incidental to a radiation image after imaging may be used. When such information cannot be acquired, region recognition processing may be performed on the radiation image to acquire information. In this case, a table in which processing on/off is associated with a region may be stored in the storage unit 42, and processing on/off may be switched with reference to the table.

In the first and second embodiments described above, both of the processed radiation image and the radiation image before processing may be displayed, and any radiation image which is used for diagnosis may be selected.

There is a case where time-dependent comparison and observation is performed using past radiation images in order to perform diagnosis of the progression or severity of a disease. In this case, a radiation image (referred to as a first radiation image) acquired through imaging without using a scattered radiation elimination grid may be compared with a radiation image (referred to as a second radiation image) acquired through imaging using a scattered radiation elimination grid. In this case, it is preferable to correct the conditions of the scattered radiation elimination processing of this embodiment according to the processing conditions when the processing for eliminating a stripe pattern due to a grid is performed on the first radiation image, and to match the image qualities of the first and second radiation images.

In the foregoing embodiments, although the scattered radiation elimination processing is performed using the radiation image acquired in the imaging device 10 which images the radiation image of the subject using the radiation detector 14, the invention is not limited thereto, and the invention can be applied even when radiation image information of a subject is stored and recorded in a storage phosphor sheet as a radiation detector shown in JP1996-266529A (JP-H08-266529A), JP1997-024039A (JP-H09-024039), or the like, and a radiation image acquired by optically reading the radiation image information from the storage phosphor sheet is used.

EXPLANATION OF REFERENCES

10: imaging device
12: X-ray source
14: radiation detector
20: control device
22: radiation source drive control unit
24: detector control unit
30: radiation image processing device
32: characteristic acquisition unit
34: scattering information acquisition unit
36: scattered radiation elimination unit
38: input unit
40: display unit
42: storage unit

What is claimed is:

1. A radiation image processing device which performs image processing on a radiation image acquired through imaging a subject with a grid for eliminating scattered radiation transmitted through the subject, the radiation image processing device comprising:
   a processor that:
   performs processing for eliminating a stripe pattern due to the used grid on the radiation image and acquires a grid-use radiation image;
   acquires a virtual grid characteristic as a characteristic of a virtual grid different from the used grid; and
   performs scattered radiation elimination processing of the grid-use radiation image based on the virtual grid characteristic,
   wherein the processor converts the grid-use radiation image for performing the scattered radiation elimination processing such that a scattered radiation component and a primary radiation component in the grid-use radiation image become to a scattered radiation component and a primary radiation component included in a radiation image acquired through imaging with a grid corresponding to the virtual grid characteristic.

2. The radiation image processing device according to claim 1, wherein the processor further:
   acquires scattered component information representing a scattered component of radiation included in the grid-use radiation image,
   wherein the scattered radiation elimination processing is performed based on the scattered component information.

3. The radiation image processing device according to claim 2,
   wherein the scattered component information is a scattered radiation content distribution in the grid-use radiation image.

4. The radiation image processing device according to claim 3,
   wherein the scattered radiation content distribution is acquired from the grid-use radiation image.

5. The radiation image processing device according to claim 4,
   wherein the scattered radiation content distribution is acquired based on at least one of information of an irradiation field in the grid-use radiation image, information about the subject, and imaging conditions at the time of the acquisition of the grid-use radiation image.

6. The radiation image processing device according to claim 1,
   wherein at least one of transmittance to the scattered radiation and transmittance to primary radiation included in radiation transmitted through the subject is acquired as the virtual grid characteristic.

7. The radiation image processing device according to claim 6,
   wherein the virtual grid characteristic is acquired by receiving a designation of the virtual grid characteristic.

8. The radiation image processing device according to claim 7,
wherein the designation of the virtual grid characteristic is received by at least one of grid information representing the type of a grid, information about the subject, and imaging conditions at the time of the acquisition of the grid-use radiation image.

9. The radiation image processing device according to claim 1,
wherein the scattered radiation elimination processing is performed on at least one frequency component among a plurality of frequency components included in the grid-use radiation image.

10. The radiation image processing device according to claim 9,
wherein frequency resolution of the grid-use radiation image is performed to acquire a frequency component of each of a plurality of frequency bands, performs the scattered radiation elimination processing on at least one frequency component among the plurality of frequency components, and synthesizes frequency components after the scattered radiation elimination processing and other frequency components to acquire a processed radiation image.

11. The radiation image processing device according to claim 10,
wherein the virtual grid characteristic is acquired for each extracted frequency component.

12. The radiation image processing device according to claim 9,
wherein a frequency component of at least one frequency band from the grid-use radiation image is extracted, the scattered radiation elimination processing on the extracted frequency component is performed, and a frequency component is added or subtracted after the processing to or from the grid-use radiation image to acquire a processed radiation image.

13. A radiation image processing method using the radiation image processing device according to claim 1 which performs image processing on a radiation image acquired through imaging a subject with a grid for eliminating scattered radiation transmitted through the subject, the radiation image processing method comprising:

performing processing for eliminating a stripe pattern due to the used grid on the radiation image and acquiring a grid-use radiation image;
acquiring a virtual grid characteristic as a characteristic of a virtual grid different from the used grid; and
performing scattered radiation elimination processing of the grid-use radiation image based on the virtual grid characteristic,
wherein the grid-use radiation image is converted for performing the scattered radiation elimination processing such that a scattered radiation component and a primary radiation component in the grid-use radiation image become to a scattered radiation component and a primary radiation component included in a radiation image acquired through imaging with a grid corresponding to the virtual grid characteristic.

14. A non-transitory storage medium storing radiation image processing program causing a computer to execute a radiation image processing method using the radiation image processing device according to claim 1 which performs image processing on a radiation image acquired through imaging a subject with a grid for eliminating scattered radiation transmitted through the subject, the radiation image processing program stored in the non-transitory storage medium comprising:

performing processing for eliminating a stripe pattern due to the used grid on the radiation image and acquiring a grid-use radiation image;
acquiring a virtual grid characteristic as a characteristic of a virtual grid different from the used grid; and
performing scattered radiation elimination processing of the grid-use radiation image based on the virtual grid characteristic,
wherein the grid-use radiation image is converted for performing the scattered radiation elimination processing such that a scattered radiation component and a primary radiation component in the grid-use radiation image become to a scattered radiation component and a primary radiation component included in a radiation image acquired through imaging with a grid corresponding to the virtual grid characteristic.

\* \* \* \* \*